(12) United States Patent
Wallenstein et al.

(10) Patent No.: US 9,017,409 B2
(45) Date of Patent: Apr. 28, 2015

(54) SPINAL INTERBODY SPACER WITH SEMI-CONSTRAINED SCREWS

(75) Inventors: Todd Wallenstein, Ashburn, VA (US); Megan E. McMullen, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 449 days.

(21) Appl. No.: 13/092,397

(22) Filed: Apr. 22, 2011

(65) Prior Publication Data
US 2012/0271423 A1 Oct. 25, 2012

(51) Int. Cl.
*A61F 2/44* (2006.01)
*A61B 17/86* (2006.01)
*A61F 2/30* (2006.01)
*A61F 2/28* (2006.01)

(52) U.S. Cl.
CPC ............ *A61F 2/447* (2013.01); *A61B 17/8685* (2013.01); *A61B 17/8615* (2013.01); *A61B 17/862* (2013.01); *A61B 17/863* (2013.01); *A61B 17/864* (2013.01); *A61B 17/8695* (2013.01); *A61F 2002/30438* (2013.01); *A61F 2002/30787* (2013.01); *A61F 2002/30904* (2013.01); *A61F 2002/4475* (2013.01); *A61F 2310/00017* (2013.01); *A61F 2310/00023* (2013.01); *A61F 2310/00029* (2013.01); *A61F 2002/2817* (2013.01); *A61F 2002/2835* (2013.01); *A61F 2002/30281* (2013.01); *A61F 2002/30507* (2013.01); *A61F 2002/30596* (2013.01); *A61F 2002/30598* (2013.01); *A61F 2002/30733* (2013.01); *A61F 2002/30774* (2013.01); *A61F 2002/30777* (2013.01); *A61F 2002/30779* (2013.01)

(58) Field of Classification Search
USPC ......... 623/17.11, 17.14–17.16; 606/288, 289, 606/290, 305, 304, 306, 319, 320
See application file for complete search history.

(56) References Cited

U.S. PATENT DOCUMENTS

| | | | |
|---|---|---|---|
| 4,259,072 A * | 3/1981 | Hirabayashi et al. | 433/173 |
| 4,611,581 A * | 9/1986 | Steffee | 606/292 |
| 5,053,036 A | 10/1991 | Perren et al. | |
| 5,084,050 A * | 1/1992 | Draenert | 606/77 |
| 5,122,133 A * | 6/1992 | Evans | 606/301 |
| 5,954,722 A | 9/1999 | Bono | |
| 6,022,352 A * | 2/2000 | Vandewalle | 606/286 |
| 6,099,531 A | 8/2000 | Bonutti | |
| 6,187,005 B1 | 2/2001 | Brace et al. | |
| 6,235,033 B1 | 5/2001 | Brace et al. | |
| 6,342,074 B1 | 1/2002 | Simpson | |
| 6,364,880 B1 | 4/2002 | Michelson | |
| 6,423,063 B1 | 7/2002 | Bonutti | |

(Continued)

*Primary Examiner* — Kevin T Truong
*Assistant Examiner* — Lynnsy Summitt
(74) *Attorney, Agent, or Firm* — Carter, DeLuca, Farrell & Schmidt, LLP

(57) ABSTRACT

An intervertebral implant system is disclosed which includes a spinal spacer for engagement between vertebrae and at least one semi-constrained bone screw assembly. The spinal spacer includes a body extending between first and second end surfaces to define opposing top and bottom vertebral engaging surfaces. The second end surface of the body includes at least one aperture formed therethrough at an angle relative to the centerline axis and a screw opening defined therethrough. The semi-constrained bone screw assembly is adapted for insertion through the screw opening and includes a shank, a head and a rod member. The rod member is fixedly engageable with the shank and moveably coupled to the head such that both the rod member and the shank are moveable with respect to the head.

18 Claims, 12 Drawing Sheets

(56) References Cited

U.S. PATENT DOCUMENTS

| | | | |
|---|---|---|---|
| 6,558,423 B1 | 5/2003 | Michelson | |
| 6,629,998 B1 * | 10/2003 | Lin | 623/17.11 |
| 6,972,019 B2 | 12/2005 | Michelson | |
| 6,984,234 B2 | 1/2006 | Bray | |
| 7,001,385 B2 | 2/2006 | Bonutti | |
| 7,033,394 B2 | 4/2006 | Michelson | |
| 7,041,135 B2 | 5/2006 | Michelson | |
| 7,074,203 B1 * | 7/2006 | Johanson et al. | 602/72 |
| 7,077,864 B2 * | 7/2006 | Byrd et al. | 623/17.11 |
| 7,175,624 B2 | 2/2007 | Konieczynski et al. | |
| 7,527,640 B2 | 5/2009 | Ziolo et al. | |
| 7,651,517 B2 | 1/2010 | Konieczynski et al. | |
| 8,114,141 B2 * | 2/2012 | Appenzeller et al. | 606/328 |
| 8,292,934 B2 * | 10/2012 | Justis et al. | 606/328 |
| 2001/0021851 A1 | 9/2001 | Eberlein et al. | |
| 2002/0042615 A1 | 4/2002 | Graf et al. | |
| 2002/0045896 A1 | 4/2002 | Michelson | |
| 2002/0128654 A1 | 9/2002 | Steger et al. | |
| 2003/0130737 A1 | 7/2003 | McGahan et al. | |
| 2004/0138662 A1 | 7/2004 | Landry et al. | |
| 2006/0100625 A1 | 5/2006 | Ralph et al. | |
| 2008/0071273 A1 * | 3/2008 | Hawkes et al. | 606/61 |
| 2008/0183293 A1 * | 7/2008 | Parry et al. | 623/17.11 |
| 2008/0234677 A1 | 9/2008 | Dahners et al. | |
| 2008/0249624 A1 | 10/2008 | Josimovic-Alasevic et al. | |
| 2008/0249625 A1 * | 10/2008 | Waugh et al. | 623/17.16 |
| 2009/0157123 A1 * | 6/2009 | Appenzeller et al. | 606/301 |
| 2009/0264937 A1 * | 10/2009 | Parrott | 606/305 |
| 2010/0087925 A1 * | 4/2010 | Kostuik et al. | 623/17.16 |
| 2010/0145460 A1 * | 6/2010 | McDonough et al. | 623/17.16 |
| 2011/0106172 A1 | 5/2011 | Wallenstein | |
| 2011/0172718 A1 * | 7/2011 | Felix et al. | 606/305 |

\* cited by examiner

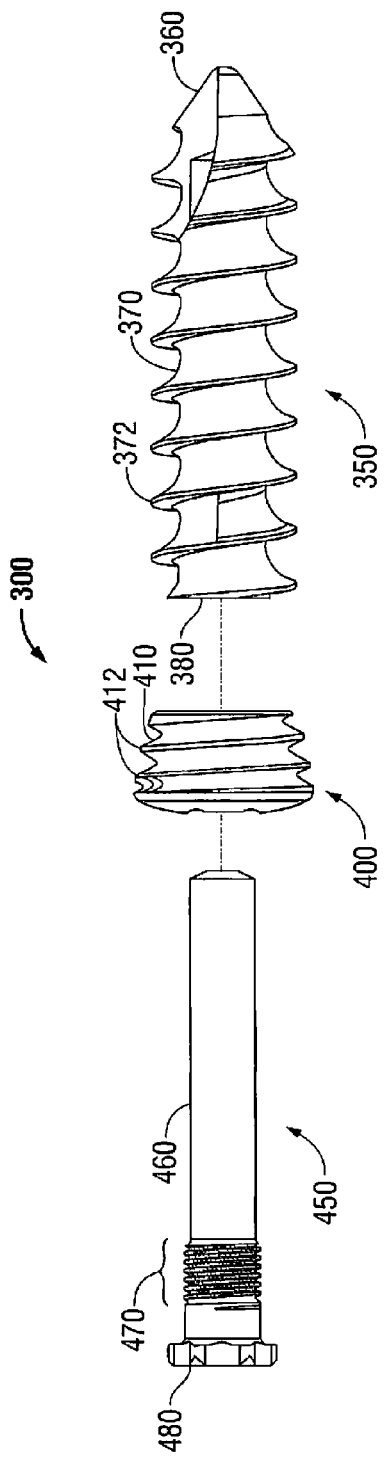
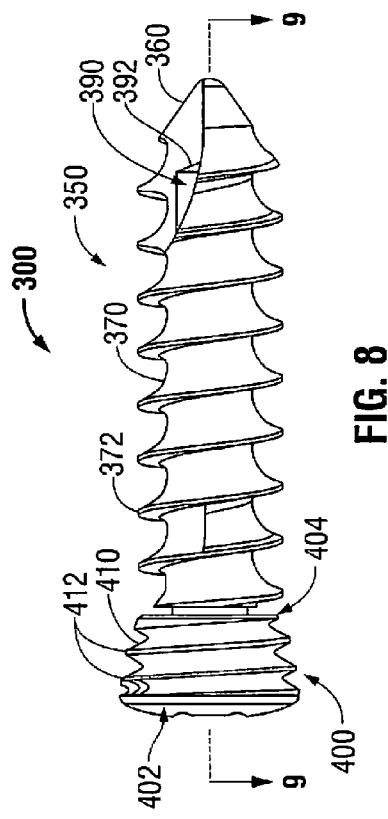

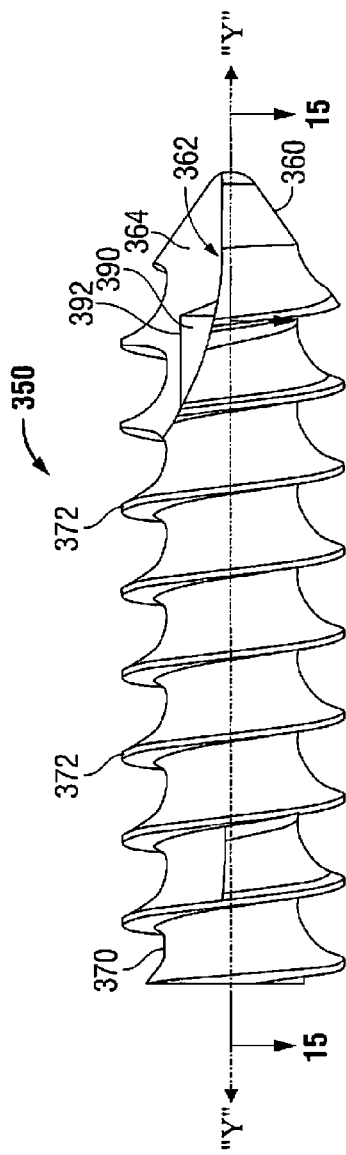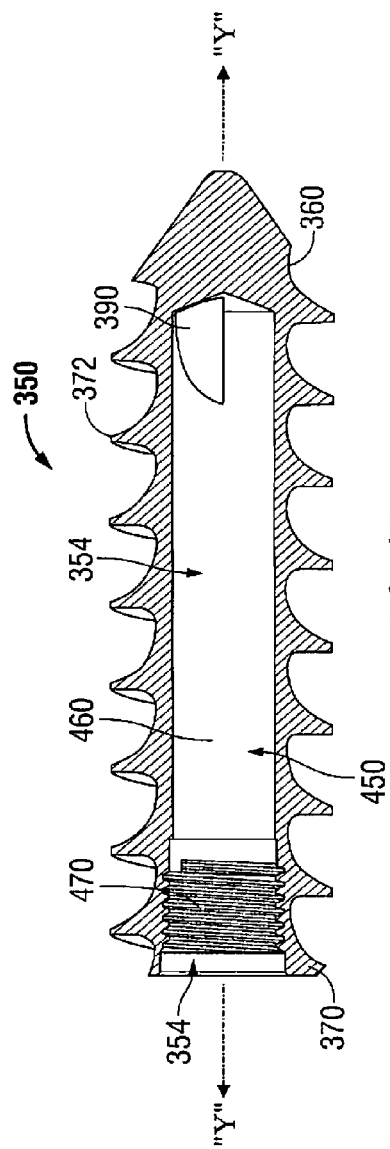

SPINAL INTERBODY SPACER WITH SEMI-CONSTRAINED SCREWS

BACKGROUND

1. Technical Field

The present disclosure relates to devices and methods for implantation between adjacent vertebrae. Specifically, the disclosure relates to a spinal interbody spacer that inhibits the collapse of the space between adjacent vertebrae after a discectomy and a semi-constrained bone screw to be used therewith.

2. Background of Related Art

The human spinal column is a highly complex structure. It includes more than twenty discrete bones, known as vertebrae, coupled sequentially to one another to house and protect critical elements of the nervous system. The cervical portion of the spine, which comprises the top of the spine up to the base of the skull, includes the first seven vertebrae.

For many reasons, such as aging and trauma, the intervertebral discs may begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. However, should the prosthetic protrude from the adjacent vertebrae and thereby contact the surrounding nerves or tissues, the patient may experience additional discomfort. In procedures for remedying this problem, a spinal plate assembly having one or more apertures and one or more bone screws is affixed to the vertebrae and oriented to inhibit such protrusion.

After a partial or complete discectomy, the normally occupied space between adjacent vertebral bodies is subject to collapse and/or misalignment due to the absence of all or a part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth has occurred. A common problem associated with the use of such a spinal plate assembly is the tendency of the bone screws to "back out" or pull away or otherwise withdraw from the bone into which they are mounted. This problem occurs, primarily, due to the normal torsional and bending motions of the body and spine or due to subsidence of the vertebrae. As the screws become loose and pull away or withdraw from the bone, the heads of the screws can rise above the surface of the plate assembly, which results in pain and discomfort for the patient or possibly the separation of the spinal plate from one or more vertebrae.

Therefore, a need exists for an intervertebral implant system that provides a desired amount of lordosis, allows for bone growth between adjacent vertebrae, maintains the space between adjacent vertebrae during bone ingrowth, prevents bone screws from becoming loose and "backing out" from the bone and resists dislocation from its implantation site.

SUMMARY

An intervertebral implant system is disclosed which provides for additional spinal flexibility when implanted to allow for normal torsional or bending motions of the spine and natural subsidence of the vertebrae. The intervertebral implant system includes a spinal spacer for engagement between vertebrae and at least one semi-constrained bone screw assembly.

The spinal spacer includes a body having a first end surface at a distal end of the body and a second end surface opposite thereto at a proximal end of the body. The body extends between the first and second end surfaces to define opposing top and bottom vertebral engaging surfaces which are substantially symmetrical about a centerline axis. The body further defines side surfaces. A hollow inner body is defined by an opening extending through the top and bottom vertebral engaging surfaces and the second end surface of the body includes at least one aperture formed therethrough at an angle relative to the centerline axis and in communication with the hollow inner body. The spinal spacer also includes at least one plate insert having a screw opening defined therethrough and configured to be mounted to the body with the screw opening substantially aligned with the at least one aperture. The plate insert is configured with a lip disposed in the screw opening configured to engage threads of a bone screw to secure the bone screw within the at least one plate insert.

The semi-constrained bone screw assembly is adapted for insertion through the screw opening of the at least one plate insert. The semi-constrained bone screw includes a shank defining a lumen extending at least partially therethrough from a proximal end thereof, a head defining a lumen therethrough and including a threaded portion configured to engage the lip of the screw opening, and a rod member configured for insertion through the lumen of the head and into the lumen of the shank. The rod member is fixedly engageable with the shank and moveably coupled to the head such that both the rod member and the shank are moveable with respect to the head.

The spinal spacer may include three plate inserts and may include one semi-constrained bone screw for each of the three plate inserts. The shank of the semi-constrained bone screw may include a helical thread formed on an outer surface of the shank to facilitate insertion into bone and the rod member is movably coupled to the head such that the shank and rod member are axially movable along a longitudinal axis of the head and pivotably movable with respect to the longitudinal axis of the head. The bone is also movable relative to the spinal spacer.

In another embodiment of the intervertebral implant system the spinal spacer includes a body having a first end surface at a distal end of the body and a second end surface opposite thereto at a proximal end of the body. The body extends between the first and second end surfaces to define opposing top and bottom surfaces and the body further defines side surfaces and a hollow open central region extending through the top and bottom vertebral engaging surfaces. The second end surface of the body includes at least one aperture formed therethrough at an angle relative to a centerline axis extending between the proximal and distal surfaces and the at least one aperture has a screw opening defined therethrough having formed therein a lip configured and dimensioned to engage threads on the head of a screw inserted through the at least one aperture. The intervertebral implant system also includes at least one semi-constrained bone screw assembly which is adapted for insertion through the screw opening of the at least one aperture. The semi-constrained bone screw includes a shank defining a lumen extending at least partially therethrough from a proximal end thereof, head defining a lumen therethrough and including a threaded portion configured to engage the lip of the screw opening, and a rod member configured for insertion through the lumen of the head and into the lumen of the shank. The rod member is fixedly engageable with the shank and moveably coupled to the head such that both the rod member and the shank are moveable with respect to the head. The spinal spacer may include three apertures and may include one semi-constrained bone screw for each of the three apertures. The shank of the semi-constrained bone screw may include a helical thread formed on an outer surface of the shank to facilitate insertion into bone and the rod member may movably coupled to the head such that the shank and rod member are axially movable along a longitudinal axis of the head and pivotably movable with respect to the longitudinal axis of the head. The bone may also be movable relative to the spinal spacer.

A method of fusing adjacent vertebrae is also disclosed. The method includes providing a spinal spacer for engagement between vertebrae. The spinal spacer includes a body having a first end surface at a distal end of the body and a second end surface opposite thereto at a proximal end of the body. The body extends between the first and second end surfaces to define opposing top and bottom vertebral engaging surfaces substantially symmetrical about a centerline axis and further defines side surfaces and a hollow inner body defined by an opening extending through the top and bottom vertebral engaging surfaces. The second end surface of the body includes at least one aperture formed therethrough at an angle relative to the centerline axis and in communication with the hollow inner body. The at least one aperture includes a screw opening defined therethrough and the screw opening includes a lip disposed therein and configured to engage threads of a bone screw to secure the bone screw within the at least one plate insert.

The method also includes providing at least one semi-constrained bone screw. The semi-constrained bone screw includes a shank defining a lumen extending at least partially therethrough from a proximal end thereof, a head defining a lumen therethrough and including a threaded portion configured to engage the lip of the screw opening of the at least one aperture, and a rod member configured for insertion through the lumen of the head and into the lumen of the shank. The rod member is fixedly engageable with the shank and moveably coupled to the head such that both the rod member and the shank are moveable with respect to the head.

The method further includes inserting the spinal spacer between the surfaces of the adjacent vertebrae and advancing a first of the at least one semi-constrained bone screws through a first of the at least one apertures defined through the second end surface of the spinal spacer at a first angle relative to the centerline axis and into a first vertebrae until the shank of the first semi-constrained bone screw engages bone and the threaded portion on the head of the first semi-constrained bone screw engages the lip of the screw opening of the first aperture to thereby secure the first semi-constrained bone screw to the bone and to the spinal spacer while allowing movement of the rod member relative to the head in both axial and radial directions.

The method may further include advancing a second semi-constrained bone screw through a second of the at least one apertures defined through the second end surface of the spinal spacer at a second angle relative to the centerline axis and into a second vertebrae adjacent the first vertebrae until the shank of the second semi-constrained bone screw engages bone and the threaded portion on the head of the second semi-constrained bone screw engages the lip of the screw opening of the second angled aperture to thereby secure the second semi-constrained bone screw to the bone and to the spinal spacer while allowing movement of the rod member relative to the head in both axial and radial directions.

The method may also include advancing a third semi-constrained bone screw through a third of the at least one apertures defined through the second end surface of the spinal spacer at the first angle relative to the centerline axis and into the first vertebrae until the shank of the third semi-constrained bone screw engages bone and the threaded portion on the head of the third semi-constrained bone screw engages the lip of the screw opening of the third angled aperture to thereby secure the third semi-constrained bone screw to the bone and to the spinal spacer while allowing movement of the rod member relative to the head in both axial and radial directions.

The spinal spacer may include at least one plate insert configured to be mounted to the body, where the screw opening of the at least one aperture is defined through the at least one plate insert and is substantially aligned with the at least one aperture.

BRIEF DESCRIPTION OF THE DRAWINGS

Embodiments of the presently disclosed spinal interbody spacer are described herein with reference to the accompanying drawings, wherein:

FIG. 7 is a side view of a semi-constrained bone screw according to an embodiment of the present disclosure with parts separated;

FIG. 8 is a side view of the bone screw of FIG. 7 as assembled for use;

FIG. 14 is a side view of the shank of the bone screw of FIG. 7;

FIG. 15 is a side, cross-sectional view of the bone screw of FIG. 7, taken along section line 15-15 of FIG. 14;

DETAILED DESCRIPTION

Figure 1:
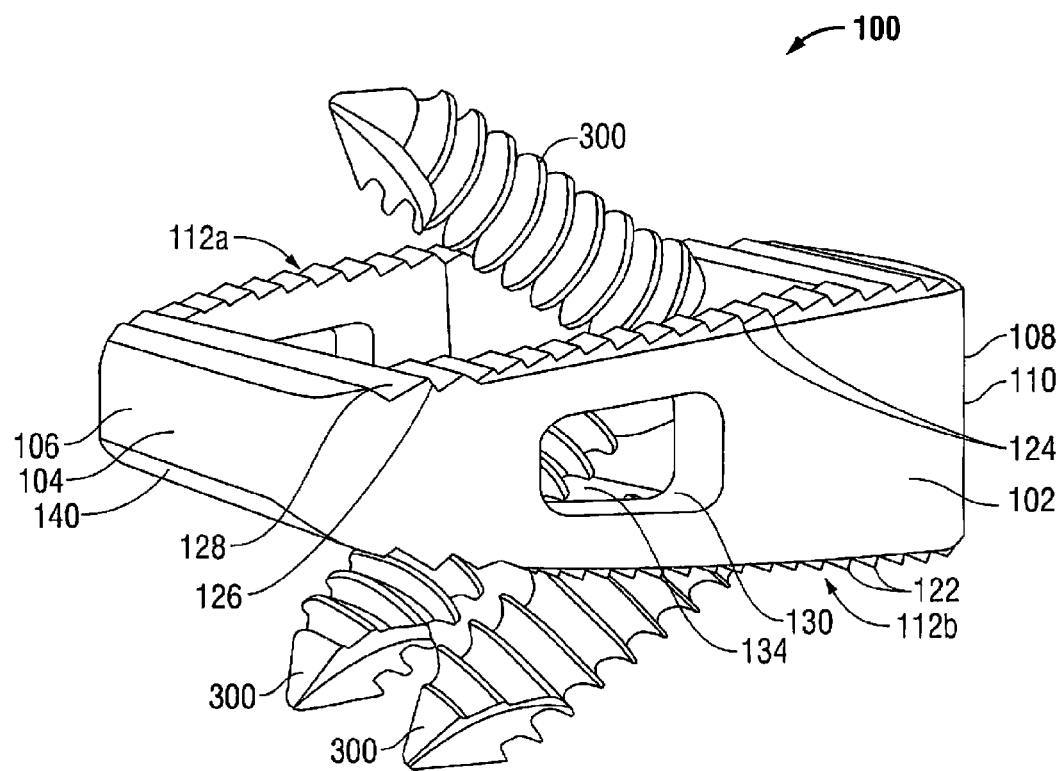
FIG. 1 is a perspective view generally from a leading or distal end of an embodiment of a spinal interbody spacer according to the present disclosure, shown assembled with bone screws.

Embodiments of the presently disclosed apparatus and method will now be described in detail with reference to the drawings, in which like reference numerals designate identical or corresponding elements in each of the several views.

In the drawings and in the description that follows, the term "proximal" refers to the portion of the device that is closest to the operator, while the term "distal" refers to the portion of the device that is furthest from the operator. Additionally, in the drawings and in the description that follows, terms such as front, rear, upper, lower, top, bottom, and the similar directional terms are used simply for convenience of description and are not intended to limit the disclosure attached hereto. In addition, the term "cephalad" is used to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Referring now to FIGS. 1-5, there is disclosed an embodiment of a spinal interbody spacer 100 for engagement between vertebrae according to the present disclosure. One such spinal interbody spacer is disclosed in U.S. patent application Ser. No. 12/247,505, which is now incorporated in its entirety herein by reference. More particularly, referring to FIGS. 1-3, spinal interbody spacer 100 includes a body 102 having a substantially contoured first end surface 104 at a distal or leading end 106 of the body 102 and a second end surface 108 opposite thereto at a proximal or trailing end 110 of the body 102. The body 102 extends between the first and second end surfaces 104 and 108 to define respective top and bottom vertebral engaging surfaces 112a, 112b, as well as opposed side surfaces 162a, 162b. The top and bottom vertebral engaging surfaces 112a, 112b are disposed opposite to one another.

Figure 2:
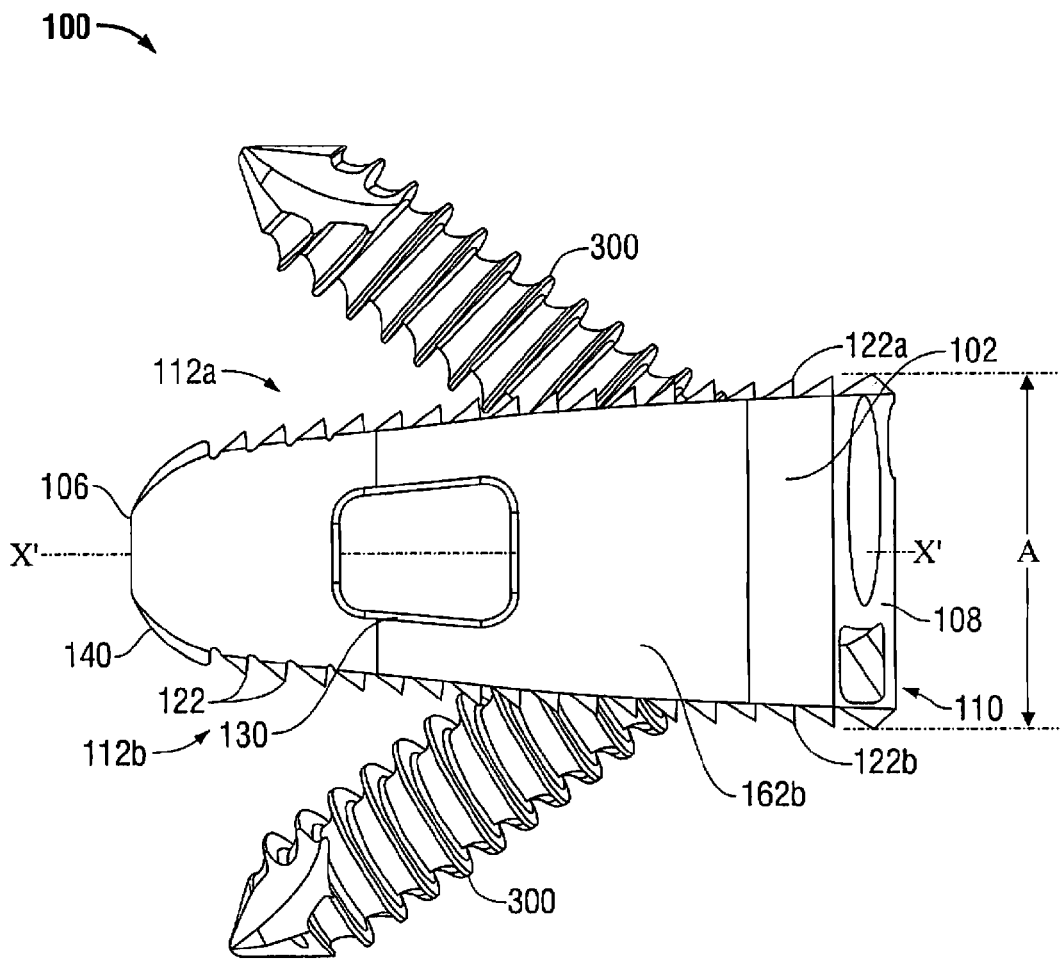
FIG. 2 is a side view of the spinal interbody spacer of FIG. 1.

As best illustrated in FIGS. 1 and 2, the body 102 is configured such that the top and bottom vertebral engaging surfaces 112a, 112b intersect the side surfaces 162a, 162b, respectively, to provide a substantially quadrilateral cross-section with rounded corners 140. As illustrated in FIGS. 1-5, the body 102 has, by way of example, a substantially rectangular cross-section, although other quadrilateral shapes such as a square are also contemplated. In addition, the cross-section shape may also be hexagonal or other suitable multi-lateral shape. The embodiments are not limited in this context.

Figure 3:
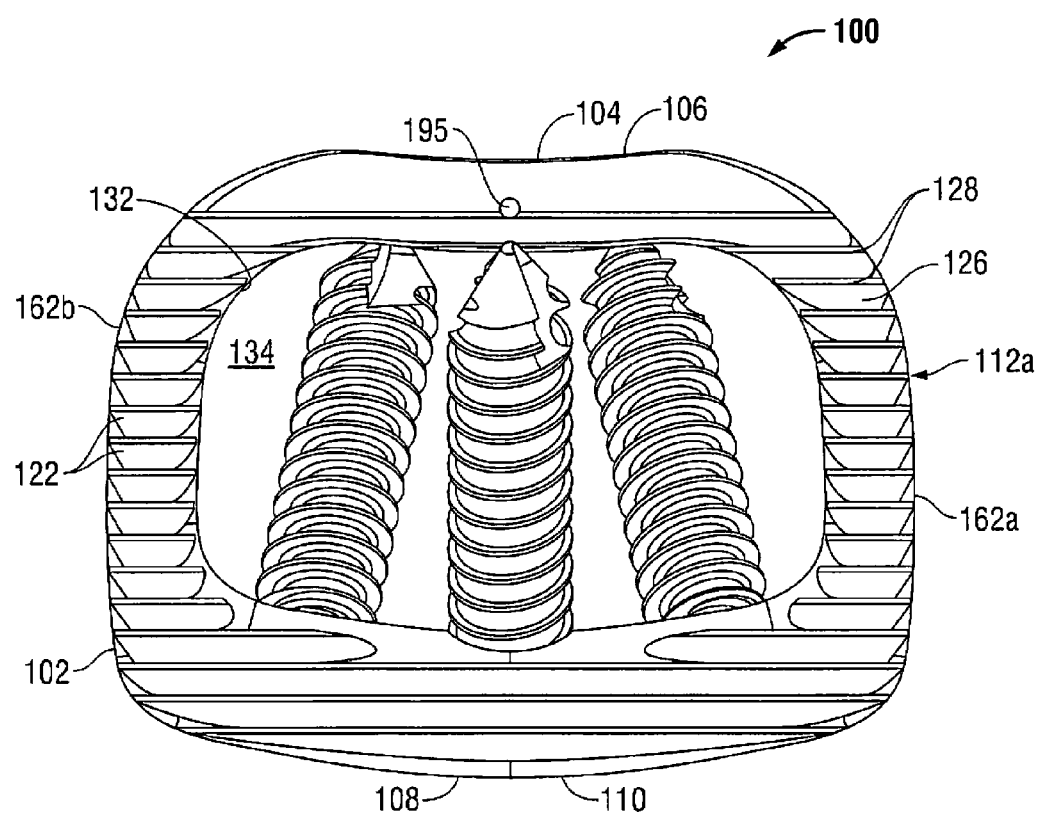
FIG. 3 is top plan view of the spinal interbody spacer of FIG. 1 showing a vertebral-engaging surface.

As best illustrated in FIG. 2, the body 102 is also configured such that the top and bottom vertebral engaging surfaces 112a, 112b have a substantially streamlined convex profile, and are configured to be substantially symmetrical around a centerline axis X-X that extends from the distal end 106 to the proximal end 110. As best illustrated in FIGS. 1 and 3, the body 102 is configured such that the side surfaces 162a, 162b have a substantially atraumatic blunt nose profile with respect to the contoured first end surface 104 and the substantially flat or planar second end surface 108. The intersection of the top and bottom surfaces 112a, 112b of the nose portion with the side surfaces 162a, 162b of the nose may be rounded to enhance the atraumatic character of the nose.

FIG. 3 illustrates a plan view of the top vertebral engaging surface 112a. As illustrated in FIGS. 1-3, surfaces 112a, 112b each have a plurality of protrusions 122 having a particular configuration. The plurality of protrusions 122 define a set of grooves 124 that face towards the proximal end 110. Each groove of the set of grooves 124 has a position along the top and bottom vertebral engaging surfaces 112a, 112b. Each groove of the set of grooves 124 includes a first face 126 that is substantially orthogonal to the top and bottom vertebral engaging surfaces 112a, 112b, i.e., to the axis X-X, at the respective position of the groove. Each groove of the set of grooves 124 includes a second opposing face 128. As best shown in FIG. 1, the second face 128 is substantially sloped or inclined with respect to the top and bottom vertebral engaging surfaces 112a, 112b so that the surfaces 126, 128 converge at the bottom of the groove. The surfaces 126, 128 may directly intersect as shown or a further surface feature, such as a flat surface portion substantially parallel to axis X-X may extend between and connect surfaces 126, 128.

Referring to FIG. 2, it can be seen that the side surfaces 162a, 162b are slightly arcuate such that the apex of the arc thereof has a greater height than both the first and second end surfaces 104 and 108, respectively. As such, the body 102 has a maximum height dimension A as measured by the distance between the tip of a protrusion 122a on the top vertebral engaging surface 112a distanced from the proximal end 110 and the tip of a protrusion 122b on the bottom vertebral engaging surface 112b correspondingly distanced from the proximal end 110.

Referring again to FIGS. 1 and 2, the body 102 may further include an aperture 130 formed therein that extends transversely across the body 102 through the side surfaces 162a, 162b. The aperture 130 may be disposed transversely under at least a portion of the top vertebral engaging surface 112a and over at least a portion of the bottom vertebral engaging surface 112b.

Referring again to FIGS. 1 and 3, the body 102 may further include an aperture 132 formed therein that may extend vertically through the body 102. The paths of the apertures 130, 132 intersect to form a hollow central region 134 (FIG. 3) of the body 102. The apertures 130, 132 and the hollow central region 134 may be filled with osteoconductive or osteoinductive materials (e.g. bone, bone chips, bone substitutes, bone growth promoting materials such as bone morphogenic proteins, etc.), or both, to enable and/or promote growth of vertebral bone therebetween to promote fusion of the adjacent spine segments and/or anchor the spinal interbody spacer 100 within the spine of a patient.

As best shown in FIG. 3, the top vertebral engaging surface 112a includes at least one aperture 195 formed therein and at least partially penetrating therethrough configured to receive an optional fiduciary insert (not shown), thus allowing the orientation of the spinal interbody spacer 100 to be determined using a number of different imaging modalities as are known in the art. This feature is particularly important when spacer 100 is made from a substantially radiolucent material (e.g. polyetheretherketone or PEEK). In embodiments, top and bottom vertebral engaging surfaces 112a, 112b may include additional apertures (not shown) at least partially penetrating therethrough to complement aperture 195.

Figure 4:
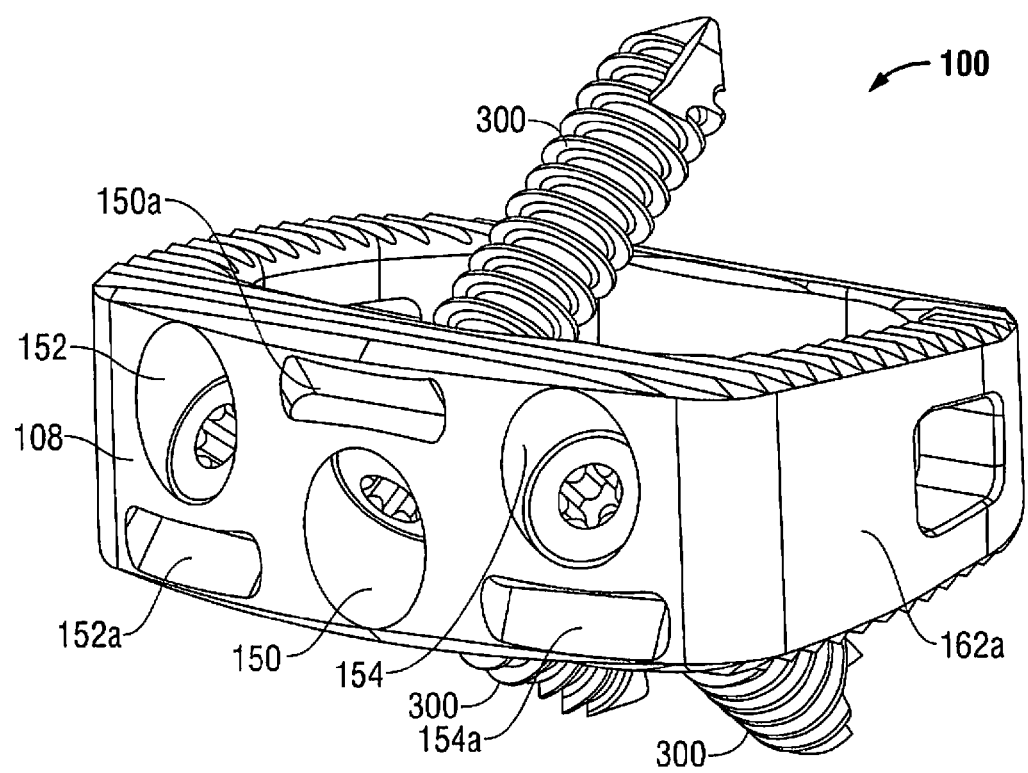
FIG. 4 is a rear elevational view of the trailing or proximal end of the spinal interbody spacer of FIG. 1.
Figure 5:
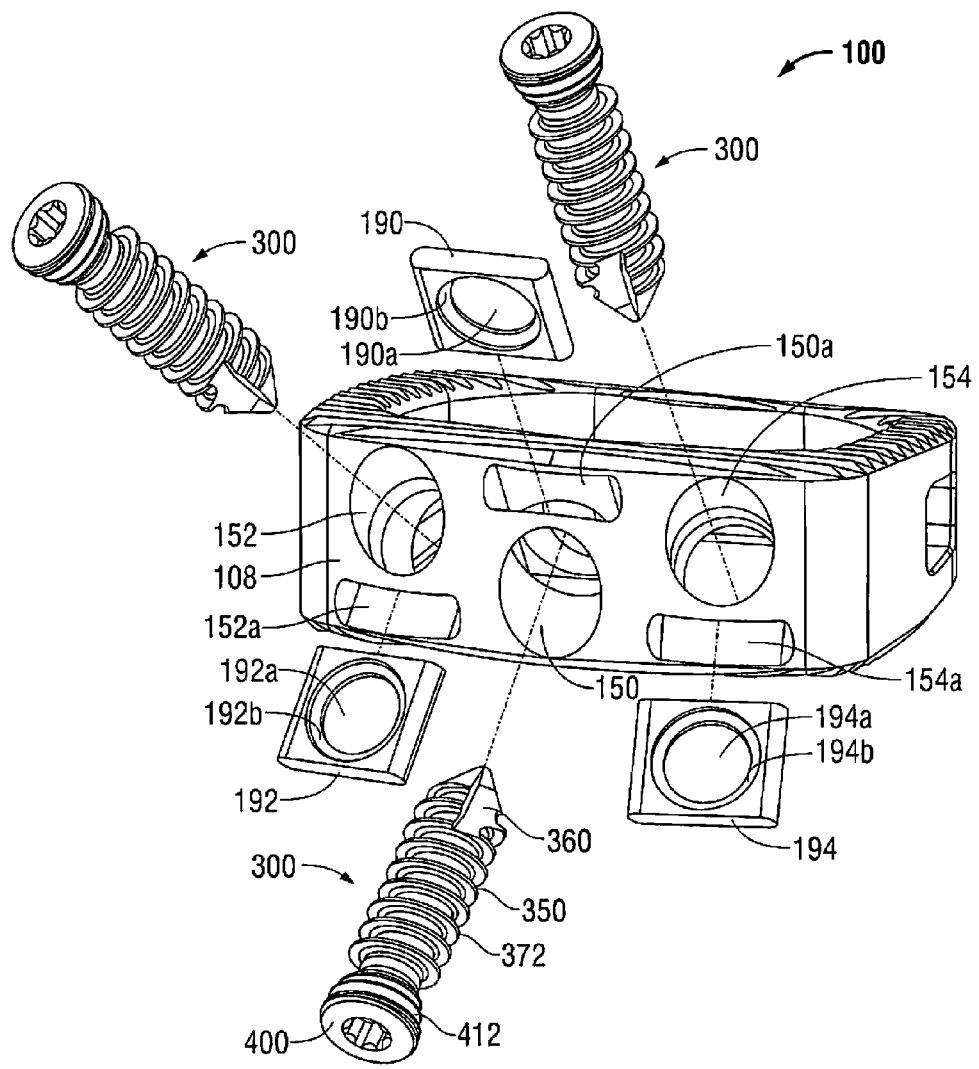
FIG. 5 is an exploded rear elevational view of the trailing or proximal end of the spinal interbody spacer of FIG. 1 with parts separated.

Referring to FIGS. 4 and 5, the proximal end 110 of the body 102 further includes a plurality of angled apertures disposed through the second end surface 108 communicating with the hollow central region 134. In the illustrated embodiment, three apertures are disposed through the second end surface 108, including one aperture 150 angled in a first direction, and two apertures 152 and 154 having a corresponding degree of angle in a second direction. In use of the spinal interbody spacer 100, the body 102 may be inverted such that aperture 150 is angled in the second direction and apertures 152, 154 are angled in the first direction. Each of angled apertures 150, 152, 154 are adapted to receive a semi-constrained bone screw 300 therethrough for insertion into bone, as will be discussed in further detail below. One such semi-constrained bone screw is disclosed in U.S. patent application Ser. No. 12/940,531, which is now incorporated in its entirety herein by reference.

Referring to FIGS. 4 and 5, the proximal end 110 of the body 102 further includes a plurality of insert slots 150a, 152a, 154a defined in the second end surface 108 communicating with angled apertures 150, 152, 154, respectively. As shown in FIG. 5, each of slots 150a, 152a, 154a are configured and dimensioned to slidably receive a respective plate insert 190, 192, 194 therein. Each of plate inserts 190, 192, 194 includes a respective screw opening 190a, 192a, 194a defined therethrough and an annular sidewall extending downward from a top surface of plate inserts 190, 192, 194 to form a corresponding lip 190b, 192b, 194b proximate a bottom surface thereof. When plate inserts 190, 192, 194 are inserted within slots 150a, 152a, 154a, screw openings 190a, 192a, 194a substantially align with corresponding apertures 150, 152, and 154 or are otherwise coincident therewith to permit bone screw 300 to be advanced therethrough. As bone screw 300 is advanced through any one of apertures 150, 152, 154 to communicate with hollow central region 134, bone screw 300 threadingly engages lips 190b, 192b, 194b to retain bone screw 300 within plate inserts 190, 192, 194, as will be discussed in further detail below. Plate inserts 190, 192, 194 are constructed of medical grade titanium. Further, the surface of plate inserts 190, 192, 194 may be anodized to provide a porous coating for absorbing a colored dye and/or to provide corrosion resistance.

Figure 6:
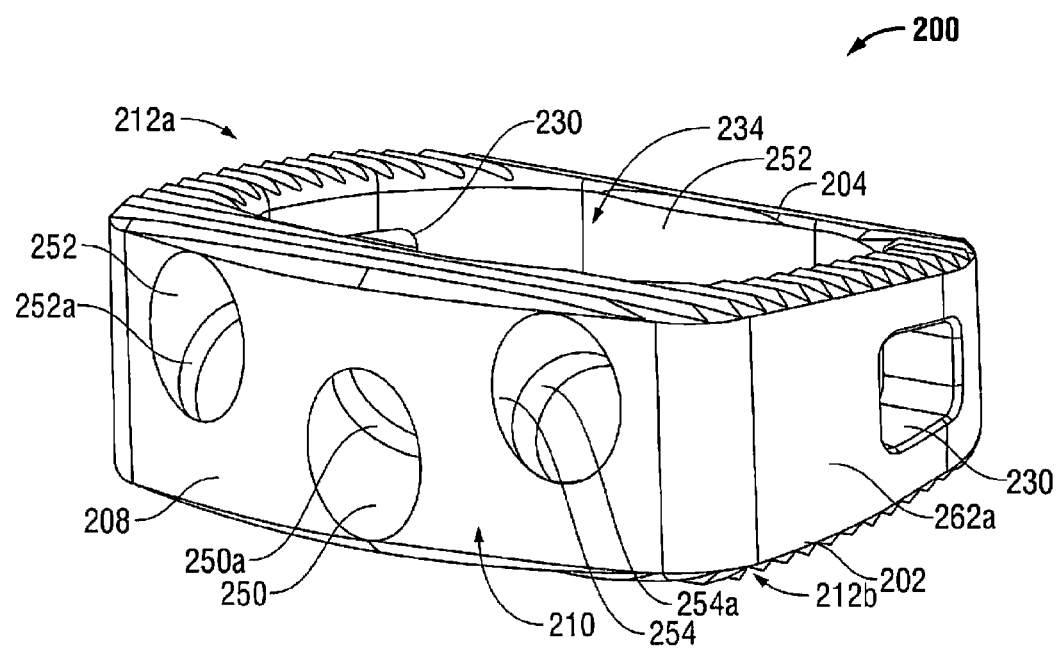
FIG. 6 is a rear elevational view of a trailing or proximal end of a spinal interbody spacer according to an embodiment of the present disclosure.

Referring now to FIG. 6, a spinal interbody spacer 200 is shown according to another embodiment of the present disclosure. Spinal interbody spacer 200 is substantially as described above with respect to spacer 100 but includes features distinct from spacer 100 which will be discussed in detail below. Spacer 200 is constructed of medical grade titanium. Further, the surface of spacer 200 may be anodized to provide a porous coating for absorbing a colored dye and/or to provide corrosion resistance. As with spacer 100, spacer 200 includes a body 202 extending between a first end surface 204 and a second end surface 208 to define respective top and bottom vertebral engaging surfaces 212a, 212b, as well as opposed side surfaces 262a, 262b. An aperture 230 through the side surfaces 262a, 262b extends transversely across the body 202 to intersect an aperture 232 extending vertically through body 202 to form a hollow central region 234. These elements function substantially as described above with respect to spacer 100 and will not be discussed in further detail herein.

Body 202 further includes a plurality of angled apertures 250, 252, 254 disposed through the second end surface 208 communicating with the hollow central region 234. In the illustrated embodiment, three apertures 250, 252, 254 are disposed through the second end surface 208, including one aperture 250 angled in a first direction, and two apertures 252 and 254 having a corresponding degree of angle in a second direction. Each of angled apertures 250, 252, 254 are adapted to receive a bone screw 300 therethrough for insertion into bone, as will be discussed in further detail below. Each angled aperture 250, 252, 254 includes an annular sidewall extending outward from a side surface thereof to form a corresponding lip 250a, 252a, 254a proximate a bottom surface of each angled aperture 250, 252, 254 and distal a top surface of each angled aperture 250, 252, 254. As a bone screw 300 is advanced through any one of apertures 250, 252, 254 to communicate with hollow central region 234, the bone screw 300 threadingly engages lips 250a, 252a, 254a to retain the bone screw 300 within apertures 250, 252, 254, as will be discussed in further detail below.

Figure 9:
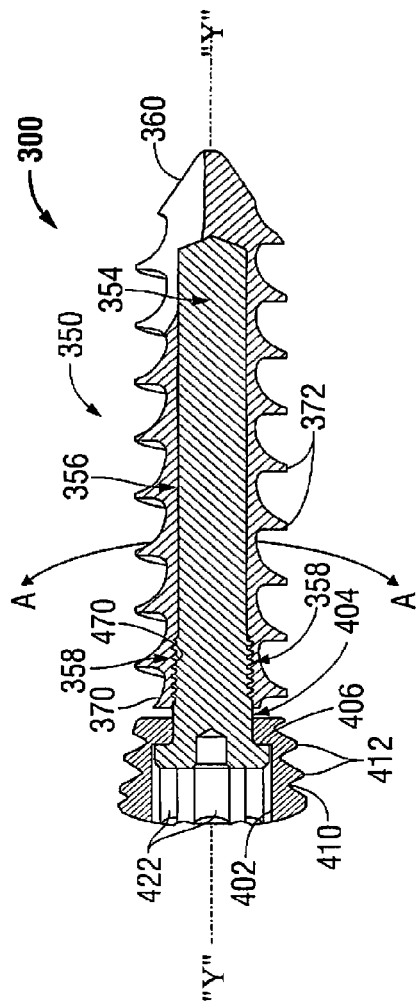
FIG. 9 is a side, cross-sectional view of the bone screw of FIG. 7 taken along section line 9-9 of FIG. 8.
Figure 10:
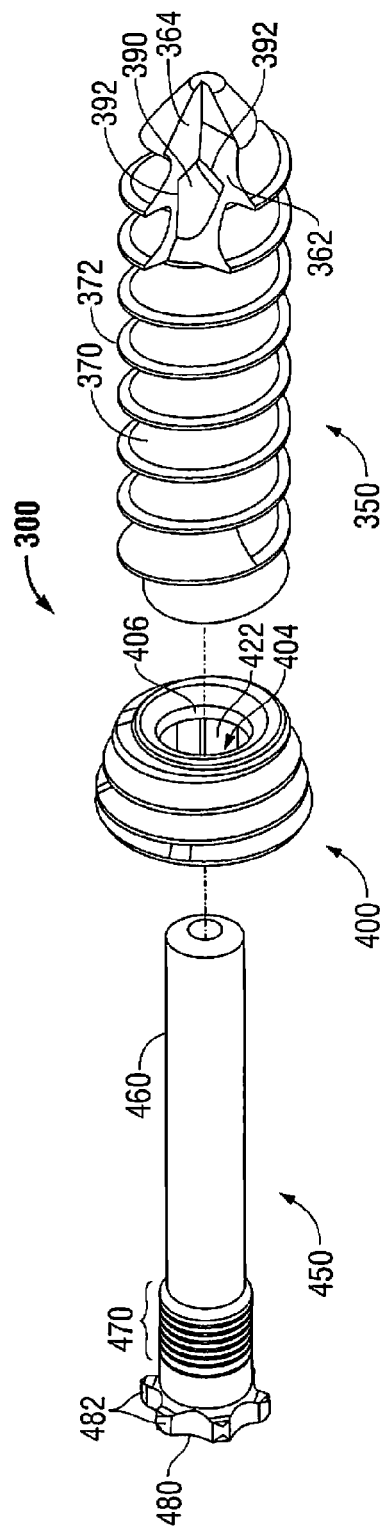
FIG. 10 is an exploded perspective view of the bone screw of FIG. 7.
Figure 12:
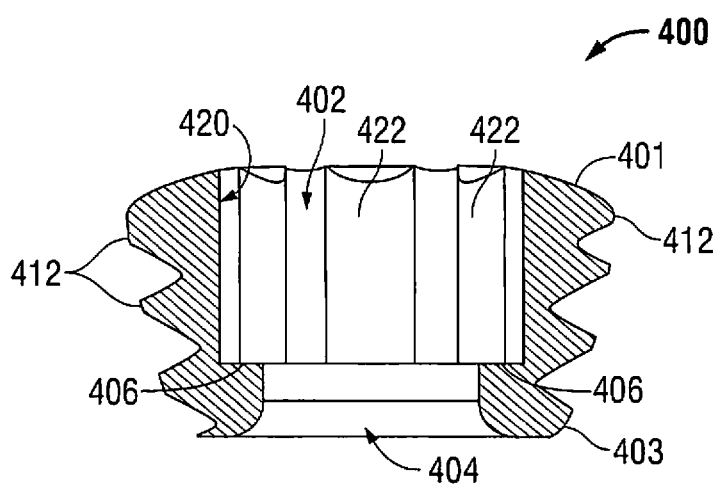
FIG. 12 is a side, cross-sectional view of the head of the bone screw of FIG. 7 taken along section line 12-12 of FIG. 11.
Figure 13A:
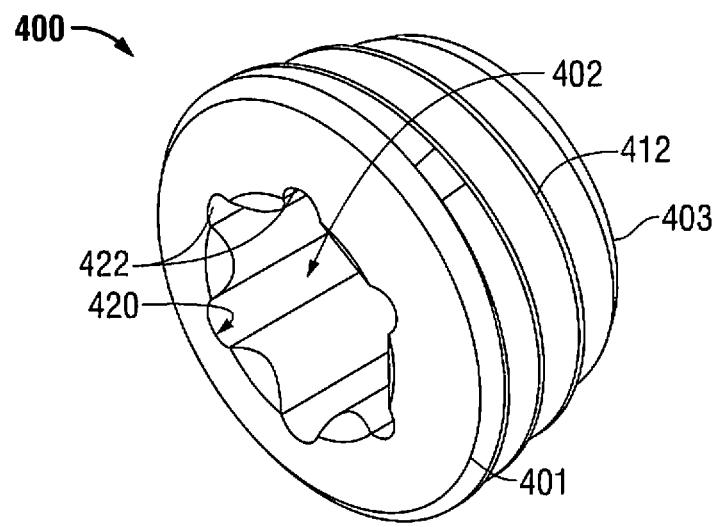
FIG. 13A is a top perspective view of the head of the bone screw of FIG. 7.

Referring initially to FIGS. 7 and 10, bone screw 300 generally includes shank 350, head 400, and rod member 450. Shank 350 includes a distal tip portion 360, an elongated body portion 370, and an open proximal end 380. Distal tip portion 360 is generally conically-shaped to facilitate insertion of bone screw 300 into bone. Elongated body portion 370 of shank 350 has a substantially uniform outer diameter and includes a continuous helical thread 372 formed thereon to allow for threaded insertion and retention of bone screw 300 within bone. A lumen 354 (FIG. 9) extends distally from the open proximal end 380 of the shank 350 partially therethrough. Head 400 of bone screw 300 is generally frustoconical in shape and includes two chambers 402 and 404 (FIG. 12), the first chamber 402 having a diameter greater than the diameter of the second chamber 404 such that a shoulder 406 is defined between the first and second chambers 402 and 404, respectively (FIG. 12). A helical threading 412 is disposed on an outer surface 410 of head 400. Further, a plurality of longitudinal slots 422 are defined on an inner surface 420 of first chamber 402 of head 400, as best seen in FIG. 13A. Rod member 450 of bone screw 300 includes a distal shaft 460, a threaded neck 470, and a proximal flange portion 480 extending radially outward from rod member 450. It is contemplated that the head 400 may be formed from a different material than the material of the shank 350 such that the bone screw 300 is formed from mixed metals/alloys. Examples of suitable materials include titanium, titanium alloys (e.g., Ti-6Al-4V), stainless steel, and cobalt chrome alloys. By way of example only, the head may be formed of titanium alloy and the shank may be formed of commercially pure titanium.

Figure 13B:
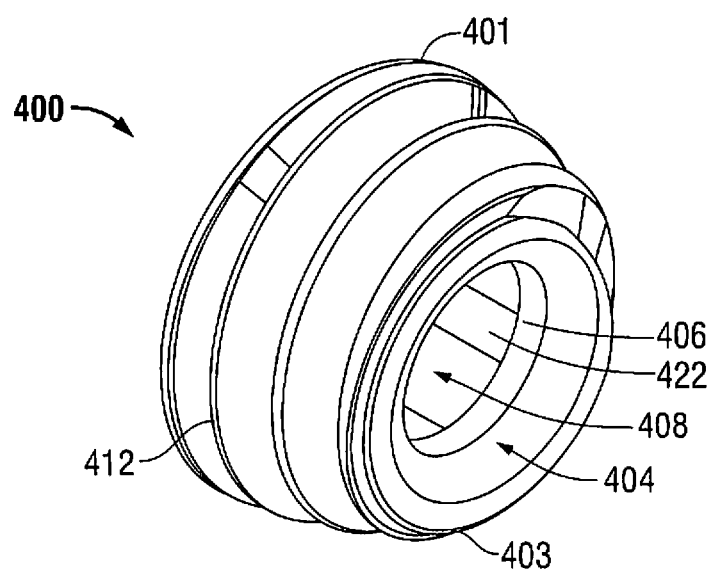
FIG. 13B is a bottom perspective view of the head of the bone screw of FIG. 7.

Referring now to FIGS. 8 and 9, helical thread 372 formed on elongated body portion 370 of shank 350 is preferably continuous and has a substantially uniform pitch. Similarly, helical thread 412 on outer surface 410 of head 400 is preferably continuous and has a substantially uniform pitch, with the pitch of thread 372 preferably being greater than the pitch of thread 412. As best seen in FIGS. 9 and 13B, shank 350 and head 400 each include a respective lumen 354, 408. Lumen 354 and the proximal opening of second chamber 404 may have a substantially equal diameter and are defined centrally within shank 350 and head 400, respectively. Inner surface 356 of shank 350 includes a threaded portion 358 disposed toward a proximal end of lumen 354, while, as discussed above, inner surface 420 of first chamber 402 of head 400 includes a plurality of longitudinal slots 422 defined therein. As mentioned above, a shoulder 406 is defined between first chamber 402 and second chamber 404.

With reference now to FIGS. 7-10, distal shaft 460 of rod member 450 is insertable through first and second chambers 402 and 404, respectively, of head 400 and into lumen 354 of shank 350. As shaft 460 is inserted further through head 400 and into lumen 354, threaded neck 470 of shaft 460 is eventually positioned adjacent threaded portion 358 of inner surface 356 of shank 350. From this position, rod member 450 and shank 350 may be rotated relative to one another to engage threads 358 with threads 470 thereby fixedly engaging shank 350 with rod member 450. At the same time, proximal flange portion 480 of rod member 450 enters first chamber 402 of head 400. As shown in the drawings, proximal flange portion 480 includes six protrusions 482 defining a generally hexagonal configuration. Slots 422 defined on inner surface 420 of first chamber 402 of head 400 define a complementary hexagonal shape. Although proximal flange portion 480 is illustrated with six protrusions 482, it is contemplated that a greater or lesser number of protrusions 482 may be formed in the proximal flange portion 480 with a corresponding number of slots 422 being formed on inner surface 420 of the head 400 such that the proximal flange portion 480 and the first chamber 402 have complementary configurations. As can be appreciated, the mating of protrusions 482 and slots 422 permits axial translation of rod member 450 with respect to head 400 along axis Y-Y, while inhibiting rotation of rod member 450 with respect to head 400 about axis Y-Y. Shoulder 406, defined between first chamber 402 and second chamber 404, acts as a stop, inhibiting rod member 450 from translating further distally through head 400. Accordingly, once rod member 450 is engaged with shank 350 via the engagement of threads 358 and 470, head 400 is retained therebetween. Although head 400 is retained between shank 350 and rod member 450, head portion 400 is axially translatable between a first position wherein shoulder 406 and proximal flange portion 480 abut one another to inhibit further axial translation in the proximal direction and a second position wherein a distal portion of head 400 contacts the proximal end 370 of shank 350, preventing further axial translation in the distal direction. Furthermore, due to the configuration of proximal flange portion 480 of rod member 450 and first chamber 402 of head 400, rod member 450 and shank 350 are also moveable a sufficient distance in the radial direction with respect to head 400 to accommodate angulation of the shank relative to the head, as described more fully below.

Referring to FIG. 9, shank 350 of bone screw 300 is angularly pivotable relative to head 400 and longitudinal axis Y-Y as indicated by directional arrows A. Since the diameter of the first chamber 402 is greater than an outside diameter of the protrusions 482 of the proximal flange 480 of the rod member 450 and the diameter of second chamber 404 increases from its proximal opening to its distal opening, as describe more fully hereinbelow, rod member 450 is pivotable relative to the head 400. A first space is defined between the outer diameter of the protrusions 482 and the corresponding slots 422, and a second space is defined between the outer diameter of the proximal flange 480 and inner surface 420 of first chamber 402. Additionally, a third space is defined between an outer surface of elongated body portion 460 (FIG. 10) and an inner surface of second chamber 404. The first, second, and third spaces permit a range of angular movement between rod member 450 and head 400 as shown by directional arrows A. Thus, when assembled as bone screw 300, shank 350 is also angularly pivotable relative to head 400 as indicated by directional arrows A. In one embodiment, shank 350 is pivotable relative to head 400 and axis Y-Y in a cone with a total range of angulation of about 10°. Other ranges of angulation are also contemplated.

Although the complementary shaped protrusions 482 and slots 422 of rod member 450 and head 400, respectively, are described and shown as defining a hexagonal configuration, it is envisioned that alternate configurations may be provided so long as rod member 450 and shank 350 are axially translatable and radially moveable, but not rotatable, with respect to head 400.

Once rod member 450 is threadably engaged with shank 350, with head 400 disposed therebetween, as described above, distal end of rod member 450 is preferably laser welded to shank 350 along flute cuts 392 of flutes 390. One or more windows may be formed through the outer surface of the shank to facilitate laser welding or joining of the rod member 450 and the shank 350. FIG. 10 illustrates a window extending through a flute, but it is also contemplated that such a welding access window may be formed at any convenient location along the shank to facilitate welding the rod to the shank. Alternatively, other techniques for securing the rod member 450 and the shank 350 are contemplated. These alternate techniques include swaging, friction fit (i.e. tapered lumen 140), etc. The laser welding of shank 350 to rod member 450 fixes screw 300 in its assembled configuration, described above, in which rod member 450 and shank 350 are fixed relative to one another, while head 400 is axially translatable and pivotably movable with respect to shank 350 and rod member 450 so as to permit angulation between the shank and the head.

Figure 11:
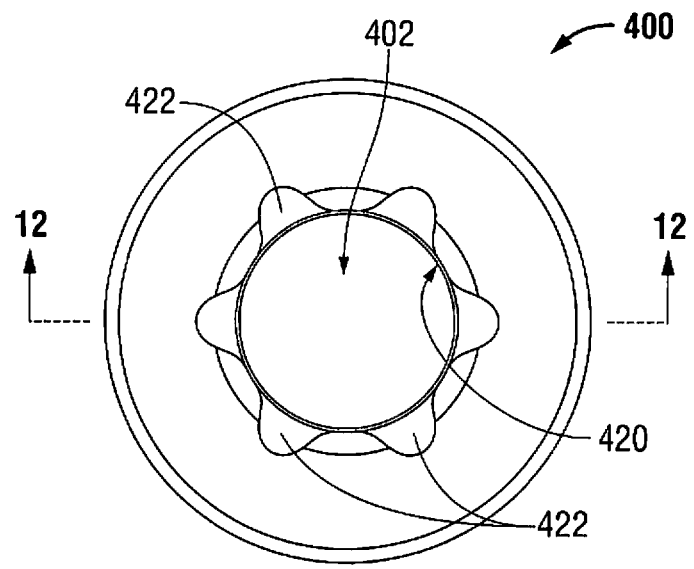
FIG. 11 is a top view of the head of the bone screw of FIG. 7.

Referring to FIGS. 11-13, and as mentioned above, head 400 includes a first chamber 402, having a first diameter, positioned at a proximal, or upper portion of head 400, and a second chamber 404, having a second diameter, positioned at a distal, or lower portion of head 400. The diameter of first chamber 402 is larger than the diameter of a proximal opening of second chamber 404 such that a shoulder 406 is defined therebetween. As shown, the diameter of the first chamber 402 is substantially uniform between the proximal and distal ends of the first chamber 402. However, it is contemplated that the proximal opening of first chamber 402 may have a larger diameter than the distal opening of first chamber 402 thus defining a generally conical or tapered configuration while maintaining the diameter of the distal opening greater than the proximal opening of second chamber 404, thereby defining the shoulder 406. A plurality of longitudinal slots 422 is defined on inner surface 420 of first chamber 402 of head 400, extending from the proximal end 401 of head 400 to shoulder 406. Accordingly, as discussed above, the complementary-shaped proximal portion 480 of rod member 450 (FIG. 10) is able to translate through first chamber 402 of head 400 within slots 422. Proximal portion 480 has a smaller diameter than first chamber 402 but a larger diameter than the proximal opening of second chamber 404 such that proximal portion 480 may translate through first chamber 402 until proximal portion 480 contacts shoulder 406, which inhibits further distal translation. The second chamber 404 has proximal and distal openings. As described hereinabove, the proximal opening of the second chamber 404 has a diameter less than the diameter of the distal opening of the first chamber 402. Further, second chamber 404 has a distal opening with a diameter that is greater than the diameter of the proximal opening of the second chamber 404. As shown, the diameter of the second chamber 404 increases from the proximal end near shoulder 406 towards the distal end and defines a tapered or chamfered opening. Head 400 is preferably constructed of a relatively hard material, such as titanium alloy. More specifically, head 400 may be constructed of Ti-6Al-4V. As best seen in FIG. 12, the width of helical threading 412 on the outer surface of head 400 tapers slightly from a proximal end 401 to a distal end 403 of head 400, such that head portion 410 is wider at the proximal end 401 as compared to the distal end 403.

Referring now to FIGS. 14-15, the distal end 360 of shank 350 may be configured such that bone screw 300 is a "self-starting" or "self-drilling" screw 300. Alternatively, distal end 360 may be configured such that bone screw 300 is a "self-tapping" bone screw 300. Further, the bone screw 300 may be configured such that the physician would drill and tap a hole in the selected bone structure prior to inserting the bone screw 300. In any configuration, distal end 360 includes first and second side walls 362 and 364 that define a flute section 390 including flute cut 392 (see FIG. 10). The first and second sidewalls 362, 364 of the flute section 390 extend from the pointed tip portion 360 to a crest of thread 372 near the distal end 360 of shank 350. The first sidewall 362 is planar and is aligned along a central longitudinal axis "Y" of the shank 350 such that first sidewall 362 is coplanar with the longitudinal axis "Y." The second side wall 364 further includes a planar portion that is parallel to the central longitudinal axis "Y" and an arcuate portion that extends proximally from the planar portion. Similarly, third and fourth side walls (not shown) are defined opposite first and second side walls 362, 364 at distal end 360 of shank 350. Although not shown in the drawings, the flute defined by the third and fourth side walls also includes a flute cut that is substantially similar to flute portion 390, and is diametrically opposed to flute portion 390 with respect to longitudinal axis "Y." As mentioned above, once rod member 450 is inserted and threadably engaged with shank 350, distal end of rod member 450 is laser welded to shank 350 along flute cuts 392 of both flutes 390. As best shown in FIG. 15, central lumen 354 extends distally from open proximal end 370 of shank 350. Lumen 354 extends only partially through shank 350 and is dimensioned to have a diameter that is slightly larger than a diameter of elongated body portion 460 of rod member 450 such that rod member 450 may be disposed therethrough, as shown in FIG. 9.

Figure 16:
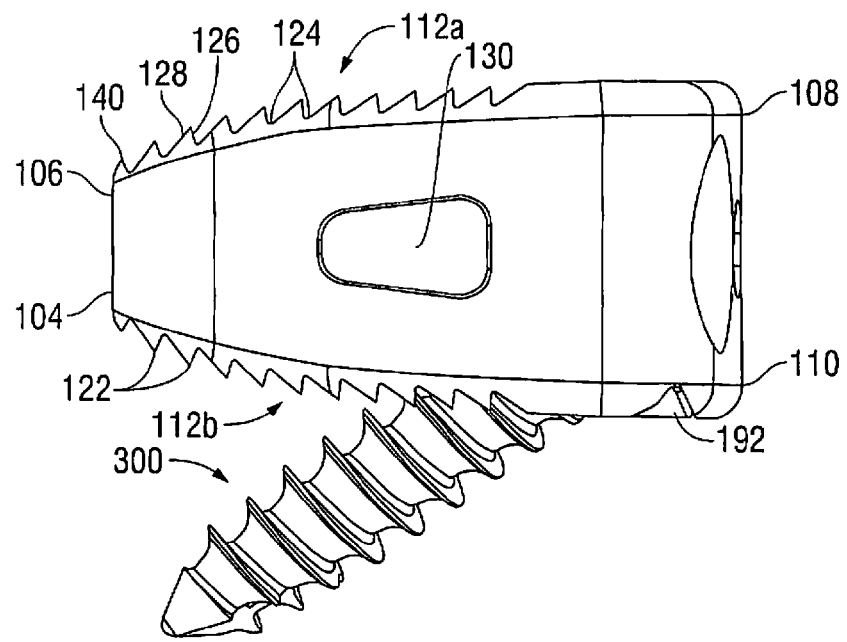
FIG. 16 is a side view of the spinal interbody spacer of FIG. 1 with a bone screw.
Figure 17:
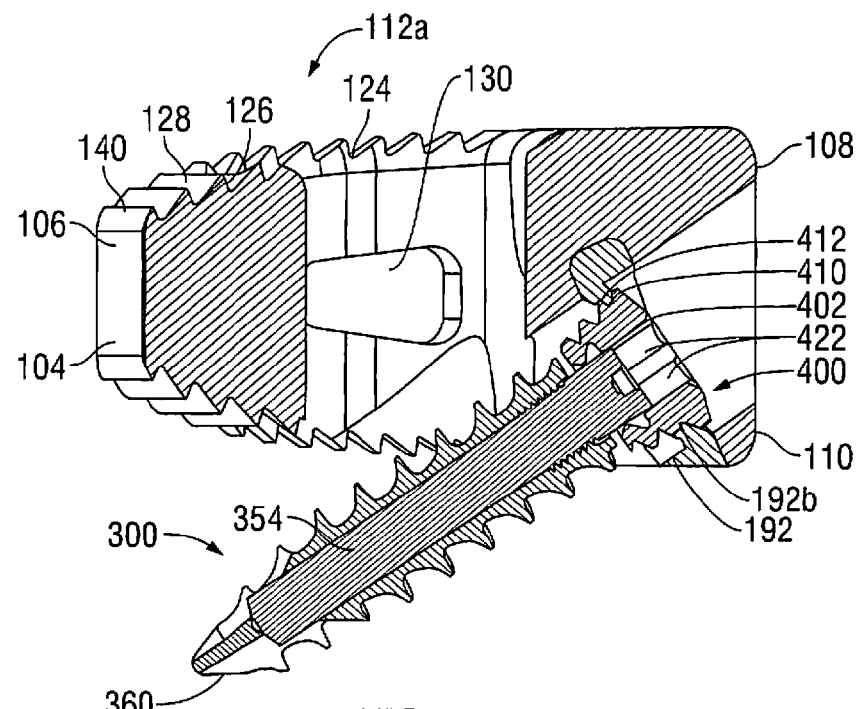
FIG. 17 is a side, cross-sectional view of the spinal interbody spacer and bone screw of FIG. 16.

Referring now to FIGS. 16-17, bone screw 300 is shown inserted through one of apertures 150, 152, 154 of spacer 100. Thread 412 of head 400 is engaged with respective lip 190b, 192b, 194b of plate 190, 192, 194 to secure head 400 to spacer 100 while rod 450 and shank 350 are able to move axially and/or angulate radially relative to head 400. Thus when threads 372 of shank 350 are engaged with the bone of an adjacent vertebrae the vertebrae and spacer 100 are not rigidly fixed together but rather are allowed to flex and bend as necessary during normal motion of the spine.

The operation of bone screw 300 in conjunction with spacer 100 will now be described in detail with reference to FIGS. 1-17. Although reference hereinbelow is made to spacer 100, it is contemplated that the same operation applies to bone screw 300 in conjunction with spacer 200 and thus, the description of such will not be repeated. As mentioned above, during assembly of screw 300, rod 450 is inserted through lumen 408 of head 400 and into lumen 354 of shank 350. Rod 450 is then engaged to shank 350 via the engagement of threads 470 with threads 358. In order to fix the screw 300 in this configuration, rod member 450 is laser welded to shank 350 at the flute cuts 392 at distal end 360 of shank 350. Once assembled, screw 300 is ready for use.

In use with spacer 100, bone screw 300 is advanced (i.e., rotated clock-wise) through apertures 150, 152, 154 toward hollow central region 134 such that distal tip portion 360 engages vertebral bone to threadingly advance thread 372 of shank 350 therein. Since the titanium makeup of plate inserts 190, 192, 194 is softer than the titanium alloy makeup of the bone screw 300, as bone screw 300 is advanced through any one of apertures 150, 152, 154 toward hollow central region 134, thread 412 of head 400 engages the corresponding lip 190b, 192b or 194b to deform the lip and secure bone screw 300 in the corresponding screw opening 190a, 192a or 194a such that bone screw 300 resists backing out of the screw opening. Further, head 400 of bone screw 300 is dimensioned to engage lips 190b, 192b, 194b to prevent further advancement of bone screw 300 toward hollow central region 134. One such screw locking arrangement is disclosed in U.S. Pat. No. 6,322,562, which is now incorporated in its entirety herein by reference.

With reference to use with spacer 200, the titanium makeup of lips 250a, 252a, 254a is softer than the titanium alloy makeup of the bone screw 300, as bone screw 300 is advanced through any one of apertures 250, 252, 254 toward hollow central region 234, thread 412 of head 400 engages the corresponding lip 150a, 152a, or 154a to deform the lip and secure bone screw 300 in the corresponding aperture 250, 252, 254 such that bone screw 300 resists backing out of the aperture. Further, head 400 of bone screw 300 is dimensioned to engage lips 150a, 152a, or 154a to prevent further advancement of bone screw 300 toward hollow central region 234.

Spinal interbody spacer 100 will now be described for use with bone screw 300. It should be understood that the following description is illustrative only in that spinal interbody spacer 100 or spinal interbody spacer 200 may be adapted for use with one or more of bone screws 300. In the use of spinal interbody spacer 100, the body 102 is inserted between adjacent vertebrae such that protrusions 122 of top and bottom vertebral engaging surfaces 112a, 112b directly engage the surface of the adjacent vertebrae to prevent spinal interbody spacer 100 from dislodging from between the adjacent vertebrae. Once the body 102 of spinal interbody spacer 100 is inserted between adjacent vertebrae, bone screws 300 are advanced through screw openings 190a, 192a, 194a and corresponding apertures 150, 152, 154 toward hollow central region 134 such that such that distal tip 360 of shank 350 is adjacent a surface of bone. A screwdriver, or driving tool (not shown) having a complementary shape, e.g. hexagonal configuration, to the shape of lumen 408 of head 400 is then engaged with head 400. The driving tool (not shown) is then rotated, thereby rotating and driving shank 350 into bone due to the pitched threading 352 disposed on shank 350. Rotation of the driving tool (not shown) causes simultaneous rotation of the head 400, rod member 450, and shank 350 due to the complementary-shaped engagement of the driving tool (not shown) with inner surface 420 of first chamber 402 of head 400 and due to the complementary-shaped engagement of the inner surface 420 with the proximal portion 480 of rod member 450. In other words, the engagement of the driving tool (not shown) and proximal portion 480 of the rod member 450 allows all the components (shank 350, head 400 and rod member 450) of screw 300 to rotate upon rotation of the driving tool (not shown). Alternatively, the physician may prepare the hole using a drill and a tap the hole prior to inserting the bone screw 300.

As best shown in FIGS. 4 and 5 and as discussed hereinabove, aperture 150 is angled in a first direction and apertures 152 and 154 are angled in a second direction such that a bone screw 300 advanced through aperture 150 is configured to anchor spinal interbody spacer 100 to one of the adjacent vertebrae and bone screws 300 advanced through apertures 152 and 154 are configured to anchor spinal interbody spacer 100 to another of the adjacent vertebrae. As the driving tool (not shown) is further rotated to further drive shank 350 into bone, distal end 401 of head 400 eventually engages the chosen aperture 150, 152, 154, thread 412 of head 400 engages the corresponding lip 190b, 192b or 194b to deform the lip and secure bone screw 300 in the corresponding screw opening 190a, 192a or 194a such that bone screw 300 resists backing out of the screw opening. Further, head portion 400 of bone screw 300 is dimensioned to engage lips 190b, 192b, 194b to prevent further advancement of bone screw 300 toward hollow central region 134. In this position, shank 350 (and thus rod member 450) is fixedly engaged with bone, and head portion 400 is fixedly engaged with spacer 100. However, due to the relationship between head 400 and shank 350 and rod member 450, wherein head 400 is axially translatable and pivotally moveable with respect to shank 350 and rod member 450, spacer 100 is still moveable with respect to bone. In other words, spacer 100 is not rigidly attached to bone, but, rather, some play exists between spacer 100 and bone even though screws 300 are sufficiently securing spacer 100 to bone. This is especially important during the natural subsidence of the vertebrae where due to motion and compression of the adjacent vertebrae a typical spinal spacer and bone screw system which is rigidly secured may either break or "back out" of the bone. Additionally, in contrast to typical spinal spacers used with fixed bone screws, the presently disclosed spacer 100 and screws 300, allows securement of the spacer 100 between adjacent vertebral bodies such that subsequent subsidence between the adjacent vertebral bodies is accommodated by the range of motion of the screws 300 relative to the spacer 100. Thus, the presently disclosed spacer 100 and screws 300 allow subsidence between adjacent vertebral bodies while maintaining secure positioning of the spacer 100 between the adjacent vertebral bodies. Thus, a certain amount of movement between adjacent vertebral bodies is accommodated while maintaining the position of the spacer 100 between adjacent vertebral bodies. This movement may be along the longitudinal axis of the spine (i.e. cephalad-caudad direction) or in a direction transverse to the longitudinal axis of the spine (i.e. medial-lateral direction) or in a direction that combines aspects of both cephalad-caudad and medial-lateral movement.

It can be understood from the foregoing disclosure of the intervertebral implant system that the system provides a spinal implant in conjunction with a semi-constrained bone screw to provide flexibility to the spine, a desired amount of lordosis, and a desired spacing between adjacent vertebral bodies, resists dislocation from the implantation site during torsional movement or subsidence, prevents screws from "backing out", and provides a path for bone ingrowth.

It will be understood that various modifications may be made to the embodiments of the presently disclosed spinal interbody spacer. By way of example only, the preferred embodiment includes a PEEK interbody implant having titanium plate inserts to lock to the bone screws. It is contemplated that all or a portion of the implant itself could be made of titanium with the lips that lockingly engage the screws formed directly into the implant, rather than as a separate insert as shown. In addition, although not preferred, it is contemplated that a thread rather than a lip may be provided in the implant hole (whether formed in the implant or as part of an insert), such that the threads on the screw head threadably engage threads provided in the implant hole. It is further contemplated that other mechanisms could be used in place of the engagement of threads on the screw head with the lip to secure the screw head to the implant. Thus, additional structures such as a cover plate (whether as a separate structure applied to the implant or pre-attached to the implant) to cover the screw head and prevent back-out, a set screw to lock the screw head to the plate and other such structures could be used in place of or in addition to the threaded screw head and lip engagement described herein and preferred. Therefore, the above description should not be construed as limiting, but merely as exemplifications of embodiments. Those skilled in the art will envision other modifications within the scope and spirit of the present disclosure.

What is claimed is:
1. An intervertebral implant system comprising:
a spinal spacer for engagement between vertebrae, the spinal spacer including a body having a first end surface at a distal end of the body and a second end surface opposite thereto at a proximal end of the body, the body extending between the first and second end surfaces to define opposing top and bottom vertebral engaging surfaces substantially symmetrical about a centerline axis, the body further defining side surfaces, a hollow inner body defined by an opening extending through the top and bottom vertebral engaging surfaces, the second end surface of the body including an aperture formed therethrough at an angle relative to the centerline axis and in communication with the hollow inner body, and a plate insert having a screw opening defined therethrough and configured to be mounted to the body with the screw opening substantially aligned with the aperture, wherein the plate insert is configured with a lip disposed in the screw opening configured to engage threads of a bone screw inserted therethrough; and
a semi-constrained bone screw adapted for insertion through the screw opening of the plate insert, the semi-constrained bone screw including a shank having a proximal surface, the shank defining a lumen extending partially therethrough from a proximal end toward a closed distal end, the lumen defining a uniform diameter along a majority of it's length thereof, a head having a distal surface, the head defining a lumen therethrough and including a threaded portion configured to engage the lip of the screw opening, and a rod member configured for insertion through the lumen of the head and into the lumen of the shank, the rod member being fixedly engageable with the shank and moveably coupled to the head such that both the rod member and the shank are moveable with respect to the head, wherein movement of the rod member and the shank when engaged with each other is limited by abutment of the proximal surface of the shank with the distal surface of the head.

2. The intervertebral implant system of claim 1, wherein the spinal spacer includes three plate inserts.

3. The intervertebral implant system of claim 2, wherein a semi-constrained bone screw is provided for each of the three plate inserts.

4. The intervertebral implant system of claim 1, wherein the shank of the semi-constrained bone screw includes a helical thread formed on an outer surface of the shank to facilitate insertion into bone.

5. The intervertebral implant system of claim 1, wherein the rod member is movably coupled to the head such that the shank and rod member are axially movable along a longitudinal axis of the head and pivotably movable with respect to the longitudinal axis of the head.

6. The intervertebral implant system of claim 5, wherein the shank and rod member are movable relative to the spinal spacer when the semi-constrained bone screw is engaged with the spinal spacer.

7. The intervertebral implant system of claim 1, wherein the lumen of the shank includes a threaded portion at a proximal end thereof for fixable engagement to the rod member.

8. The intervertebral implant system of claim 7, wherein the rod member includes a threaded neck for fixable engagement with the threaded portion of the lumen of the shank.

9. An intervertebral implant system comprising:
a spinal spacer for engagement between vertebrae, the spinal spacer including a body having a first end surface at a distal end of the body and a second end surface opposite thereto at a proximal end of the body, the body extending between the first and second end surfaces to define opposing top and bottom vertebral engaging surfaces, the body further defining side surfaces and a hollow open central region extending through the top and bottom vertebral engaging surfaces, the second end surface of the body including an aperture formed therethrough at an angle relative to a centerline axis extending between the proximal and distal surfaces, the aperture having a screw opening defined therethrough, the screw opening having a lip formed therein, the lip configured and dimensioned to engage threads on the head of a screw inserted through the aperture; and
a semi-constrained bone screw adapted for insertion through the screw opening of the aperture, the semi-constrained bone screw including a shank having a proximal surface, the shank defining a lumen extending partially therethrough from a proximal end toward a closed distal end, the lumen defining a uniform diameter along a majority of it's length thereof, a head having a distal surface, the head defining a lumen therethrough and including a threaded portion configured to engage the lip of the screw opening, and a rod member configured for insertion through the lumen of the head and into the lumen of the shank, the rod member being fixedly engageable with a threaded portion of the shank and moveably coupled to the head such that both the rod member and the shank are moveable with respect to the head, wherein movement of the rod member and the shank when engaged with each other is limited by abutment of the proximal surface of the shank with the distal surface of the head.

10. The intervertebral implant system of claim 9, wherein the spinal spacer includes three apertures.

11. The intervertebral implant system of claim 10, wherein a semi-constrained bone screw is provided for each of the three apertures.

12. The intervertebral implant system of claim 9, wherein the shank of the semi-constrained bone screw includes a helical thread formed on an outer surface of the shank to facilitate insertion into bone.

13. The intervertebral implant system of claim 9, wherein the rod member is movably coupled to the head such that the shank and rod member are axially movable along a longitudinal axis of the head and pivotably movable with respect to the longitudinal axis of the head.

14. The intervertebral implant system of claim 13, wherein the shank and rod member are movable relative to the spinal spacer when the semi-constrained bone screw is engaged with the spinal spacer.

15. A method of fusing adjacent vertebrae, comprising:
providing a spinal spacer for engagement between vertebrae, the spinal spacer including a body having a first end surface at a distal end of the body and a second end surface opposite thereto at a proximal end of the body, the body extending between the first and second end surfaces to define opposing top and bottom vertebral engaging surfaces substantially symmetrical about a centerline axis, the body further defining side surfaces, a hollow inner body defined by an opening extending through the top and bottom vertebral engaging surfaces, the second end surface of the body including an aperture formed therethrough at an angle relative to the centerline axis and in communication with the hollow inner body, the aperture including a screw opening defined therethrough, the screw opening including a lip disposed therein and configured to engage threads of a bone screw inserted through the aperture;
providing a semi-constrained bone screw, the semi-constrained bone screw including a shank having a proximal surface, the shank defining a lumen extending partially therethrough from a proximal end toward a closed distal end, the lumen defining a uniform diameter along a majority of it's length thereof, a head having a distal surface, the head defining a lumen therethrough and including a threaded portion configured to engage the lip of the screw opening of the aperture, and a rod member configured for insertion through the lumen of the head and into the lumen of the shank, the rod member being fixedly engageable with the shank and moveably coupled to the head such that both the rod member and the shank are moveable with respect to the head, wherein movement of the rod member and the shank when engaged with each other is limited by abutment of the proximal surface of the shank with the distal surface of the head;
inserting the spinal spacer between the surfaces of the adjacent vertebrae; and
advancing the semi-constrained bone screw through the aperture defined through the second end surface of the spinal spacer at a first angle relative to the centerline axis and into a first vertebrae until the shank of the semi-constrained bone screw engages bone and the threaded portion on the head of the semi-constrained bone screw engages the lip of the screw opening of the aperture to secure the semi-constrained bone screw to the bone and to the spinal spacer while allowing movement of the rod member relative to the head in both axial and radial directions.

16. The method of claim 15, further comprising advancing a second semi-constrained bone screw through a second aperture defined through the second end surface of the spinal spacer at a second angle relative to the centerline axis and into a second vertebrae adjacent the first vertebrae until the shank of the second semi-constrained bone screw engages bone and the threaded portion on the head of the second semi-constrained bone screw engages the lip of the screw opening of the second angled aperture to secure the second semi-constrained bone screw to the bone and to the spinal spacer while allowing movement of the rod member relative to the head in both axial and radial directions.

17. The method of claim 16, further comprising advancing a third semi-constrained bone screw through a third aperture defined through the second end surface of the spinal spacer at the first angle relative to the centerline axis and into the first vertebrae until the shank of the third semi-constrained bone screw engages bone and the threaded portion on the head of the third semi-constrained bone screw engages the lip of the screw opening of the third angled aperture to secure the third semi-constrained bone screw to the bone and to the spinal spacer while allowing movement of the rod member relative to the head in both axial and radial directions.

18. The method of claim 15, wherein providing a spinal spacer includes the spinal spacer further including a plate insert configured to be mounted to the body, a screw opening of the plate insert being substantially aligned with the aperture.

* * * * *